United States Patent
Bornzin et al.

(10) Patent No.: US 11,951,319 B2
(45) Date of Patent: Apr. 9, 2024

(54) SYSTEMS AND METHODS FOR APPLYING ANTI-TACHYCARDIA PACING USING SUBCUTANEOUS IMPLANTABLE CARDIOVERTER-DEFIBRILLATORS

(71) Applicant: PACESETTER, INC., Sylmar, CA (US)

(72) Inventors: Gene A. Bornzin, Simi Valley, CA (US); Xiaoyi Min, Simi Valley, CA (US); Wenwen Li, Stevenson Ranch, CA (US); Stuart Rosenberg, Castaic, CA (US); Kyungmoo Ryu, Palmdale, CA (US); Alexander Bornzin, Simi Valley, CA (US); Leyla Sabet, Los Angeles, CA (US); Shubha Asopa, Valencia, CA (US); Xing Pei, Thousand Oaks, CA (US)

(73) Assignee: Pacesetter, Inc., Sylmar (CA)

( * ) Notice: Subject to any disclaimer, the term of this patent is extended or adjusted under 35 U.S.C. 154(b) by 716 days.

(21) Appl. No.: 16/057,605

(22) Filed: Aug. 7, 2018

(65) Prior Publication Data
US 2020/0046991 A1 Feb. 13, 2020

(51) Int. Cl.
| | | |
|---|---|---|
| A61N 1/39 | (2006.01) | |
| A61N 1/05 | (2006.01) | |
| A61N 1/362 | (2006.01) | |
| A61N 1/375 | (2006.01) | |

(52) U.S. Cl.
CPC ....... *A61N 1/39622* (2017.08); *A61N 1/0587* (2013.01); *A61N 1/3622* (2013.01); *A61N 1/3756* (2013.01)

(58) Field of Classification Search
CPC .............. A61N 1/39622; A61N 1/0587; A61N 1/3622; A61N 1/3756
See application file for complete search history.

(56) References Cited

U.S. PATENT DOCUMENTS

| | | | |
|---|---|---|---|
| 2003/0036778 A1 | 2/2003 | Ostroff et al. | |
| 2003/0204210 A1* | 10/2003 | Ousdigian | A61N 1/39622 607/14 |
| 2004/0225332 A1 | 11/2004 | Gebhardt et al. | |
| 2006/0224195 A1* | 10/2006 | Sharma | A61N 1/39622 607/5 |

(Continued)

OTHER PUBLICATIONS

Communication pursuant to Rules 161(1) and 162 EPC for corresponding EP . Application No. 19755751.5-1122 dated Mar. 16, 2021 (3 pages).

(Continued)

*Primary Examiner* — Pamela M. Bays
(74) *Attorney, Agent, or Firm* — Dean D. Small; The Small Patent Law Group, LLC (57) ABSTRACT

The present disclosure provides systems and methods for applying anti-tachycardia pacing (ATP) using subcutaneous implantable cardioverter-defibrillators (SICDs). An SICD implantable in a subject includes a case including a controller, and at least one conductive lead extending from the case. The at least one conductive lead includes a plurality of coil electrodes, wherein the SICD is configured, via the controller, to apply anti-tachycardia pacing (ATP) to the subject using the at least one conductive lead.

22 Claims, 7 Drawing Sheets

(56) References Cited

U.S. PATENT DOCUMENTS

| | | | |
|---|---|---|---|
| 2008/0046014 A1* | 2/2008 | Bardy | A61N 1/3956 607/4 |
| 2008/0071318 A1* | 3/2008 | Brooke | A61N 1/3712 607/28 |
| 2009/0043352 A1* | 2/2009 | Brooke | A61N 1/36842 607/28 |
| 2010/0069985 A1* | 3/2010 | Stahmann | A61N 1/3627 607/9 |
| 2012/0130220 A1* | 5/2012 | Maskara | A61B 5/287 600/374 |
| 2012/0197329 A1* | 8/2012 | Bardy | A61N 1/3968 607/6 |
| 2014/0180351 A1* | 6/2014 | Gilman | A61N 1/36585 607/4 |
| 2014/0330325 A1 | 11/2014 | Thompson-Nauman et al. | |
| 2014/0350621 A1* | 11/2014 | Gunderson | A61N 1/3925 607/7 |
| 2015/0306410 A1 | 10/2015 | Marchall et al. | |
| 2016/0030743 A1* | 2/2016 | Kaiser | A61N 1/36514 607/14 |
| 2016/0121130 A1* | 5/2016 | Cinbis | A61N 1/0587 607/4 |
| 2017/0266442 A1* | 9/2017 | Jackson | A61B 5/363 |
| 2017/0312516 A1* | 11/2017 | Jackson | A61N 1/3622 |
| 2018/0264270 A1* | 9/2018 | Koop | A61N 1/3987 |

OTHER PUBLICATIONS

International Preliminary Report on Patentability for PCT Application No. PCT/US2019/045243 dated Feb. 9, 2021 (10 pages).

First Office Action for related CN App No. 201980051591.6 dated Sep. 26, 2023 (30 pages).

\* cited by examiner

SYSTEMS AND METHODS FOR APPLYING ANTI-TACHYCARDIA PACING USING SUBCUTANEOUS IMPLANTABLE CARDIOVERTER-DEFIBRILLATORS

A. FIELD OF THE DISCLOSURE

The present disclosure relates generally to pacing therapy, and more particularly to applying anti-tachycardia pacing using a subcutaneous implantable cardioverter-defibrillator.

B. BACKGROUND ART

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats, and the valves regulating blood flow may develop leaks, allowing regurgitation or backflow of blood. The impairment of arterial circulation deprives vital organs of oxygen and nutrients. Fatigue, weakness, and inability to carry out daily tasks may result. Not all HF patients suffer debilitating symptoms immediately. Some may live actively for years. Yet, with few exceptions, the disease is relentlessly progressive. As HF progresses, it tends to become increasingly difficult to manage.

Heart failure may result in patients experiencing ventricular arrhythmias, such as ventricular tachycardia (VT). VT may be treated by ablation and/or pacing.

Subcutaneous implantable cardioverter-defibrillators (SICDs) are a type of implantable cardiac device (ICD) generally used in patients who do not require cardiac pacing. This pacing limitation, however, prevents a potentially large pool of patients from getting an SICD. Although it has been suggested that leadless pacemakers may be used in conjunction with SICDs to support the needs of patients who require pacing, leadless pacemakers require an additional implantation procedure and may be relatively expensive.

Accordingly, it would be desirable to provide an SICD capable of treating VT by applying pacing.

BRIEF SUMMARY OF THE DISCLOSURE

In one embodiment, the present disclosure is directed to a subcutaneous implantable cardioverter-defibrillator (SICD) implantable in a subject. The SICD includes a case including a controller, and at least one conductive lead extending from the case, the at least one conductive lead including a plurality of coil electrodes, wherein the SICD is configured, via the controller, to apply anti-tachycardia pacing (ATP) to the subject using the at least one conductive lead.

In another embodiment, the present disclosure is directed to a method of assembling a subcutaneous implantable cardioverter-defibrillator (SICD). The method includes coupling at least one conductive lead to a case, the at least one conductive lead including a plurality of coil electrodes. The method further includes installing a controller in the case, the controller configured to cause the SICD to apply anti-tachycardia pacing (ATP) to the subject using the at least one conductive lead.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The systems and methods described herein facilitate treating ventricular tachycardia (VT) by applying anti-tachycardia pacing (ATP) using a subcutaneous implantable cardioverter-defibrillator (SICD). That is, as described herein, the electrodes of an SICD may be used to treat patients that experience occasional VT. In some embodiments, the electrodes of the SICD may also be used to apply high voltage (HV) therapy.

Figure 1:
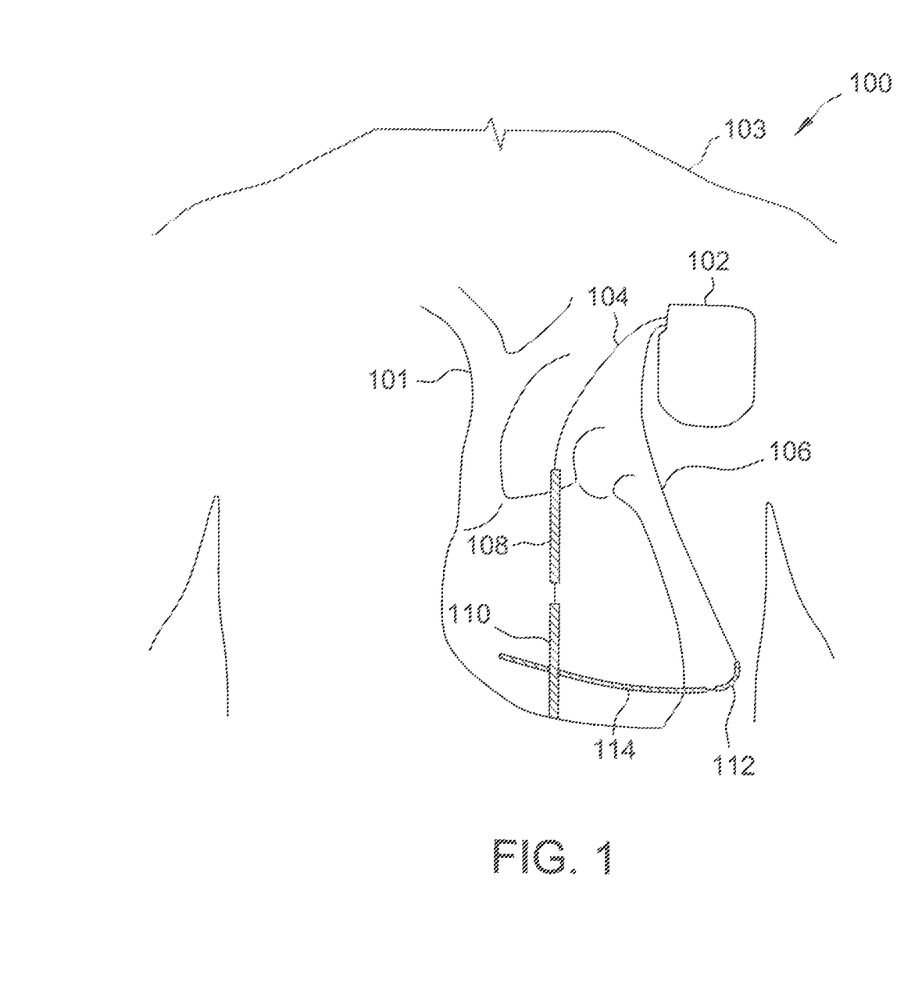
FIG. 1 is a schematic diagram of one embodiment of an exemplary SICD system that may be used to terminate VT in a heart of a subject.
Figure 2:
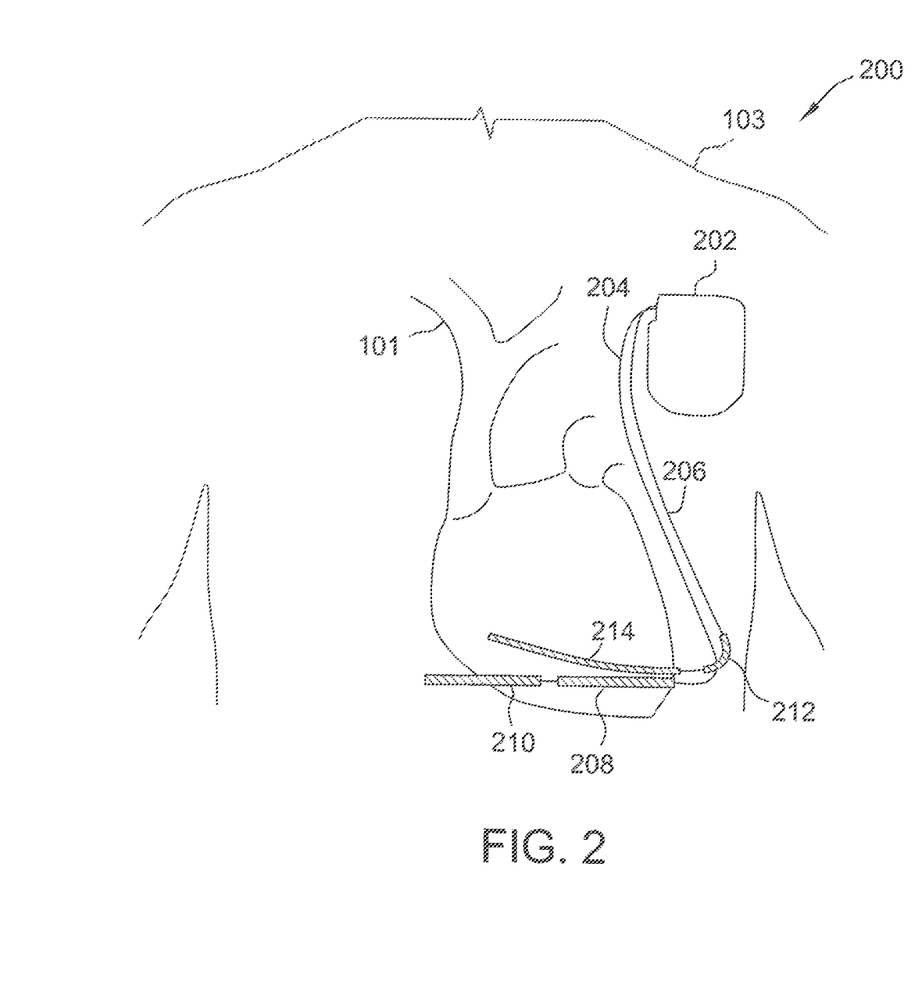
FIG. 2 is a schematic diagram of one embodiment of an exemplary SICD system that may be used to terminate VT in a heart of a subject.
Figure 3:
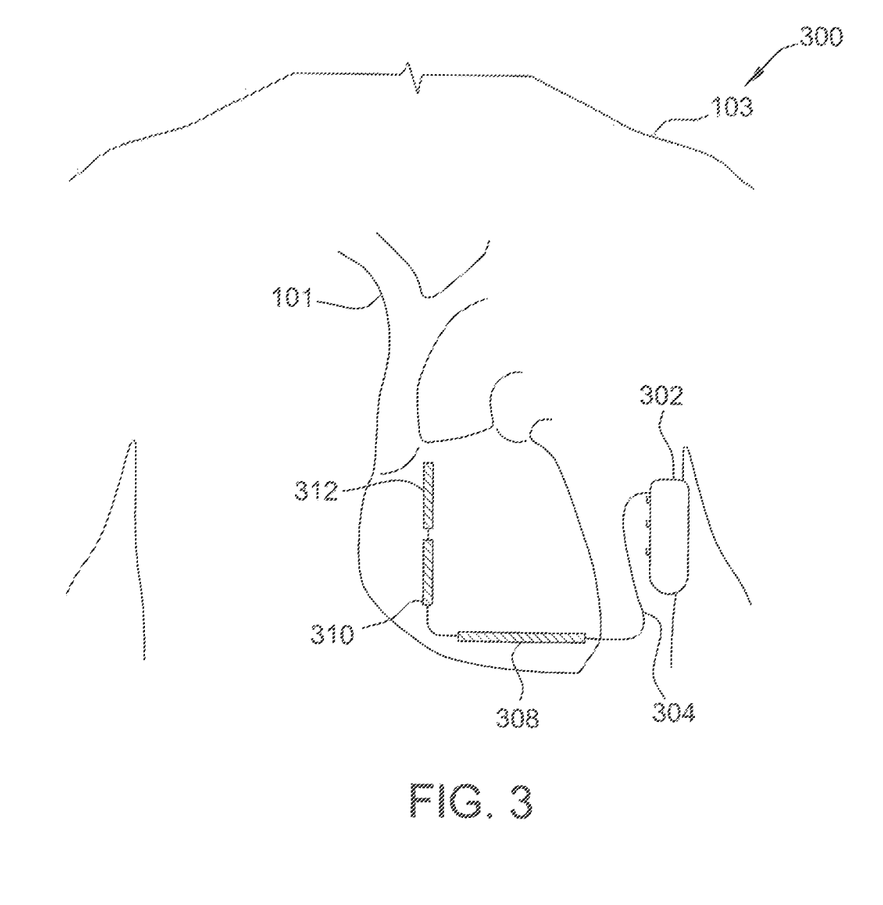
FIG. 3 is a schematic diagram of one embodiment of an exemplary SICD system that may be used to terminate VT in a heart of a subject.

FIGS. 1-3 are schematic diagrams of different embodiments of an exemplary subcutaneous implantable cardioverter defibrillator (SICD) system that may be used to apply ATP to facilitate treating VT. The embodiments shown in FIGS. 1-3 have been demonstrated, using computer modeling, to have relatively low defibrillation thresholds (DFTs) (i.e., the minimum amount of energy needed to return the heart to normal rhythm from cardiac dysrhythmia). For example, the embodiments shown in FIGS. 1-3 may have DFTs from approximately 16 to 18 Joules (J). As described herein, the defibrillation electrodes in these SICD systems may be adapted to perform subcutaneous ATP. In some embodiments, linear defibrillation coils are divided into two portions (e.g., halves) to perform ATP from each partial coil or to perform combined ATP. The delivery of the ATP (and sensing of the subsequent evoked response, etc.) is controlled by a controller (e.g., a microprocessor) installed in the case of these SICD systems.

In the embodiments described herein, ATP may be performed using pulses having an amplitude corresponding to a relatively small supra-threshold margin (e.g., approximately 1.2 times the DFT) at relatively large pulse widths (e.g., from approximately 4 to 40 milliseconds (ms)). These pulses may be minimized to reduce skeletal muscle stimulation in the subject. For example, pulses in the 20 to 200 milliamp (mA) range may be driven into a 50 ohm (0) load using only approximately 2 to 10 volts (V).

In some embodiments, larger pacing pulses may be used to capture more of the subject's heart, which may increase the probability of a single ATP pulse (or relatively few ATP pulses) terminating VT. This facilitates treating VT without using high voltage defibrillation pulses.

In the following description, with respect to the embodiments shown in FIGS. 1-3, several possible vectors (i.e., electrode combinations) for subcutaneous ATP are recommended, along with non-pacing electrode combinations that may be used for detecting the evoked response. However, those of skill in the art will appreciate that the pacing and evoked response electrode combinations identified herein are merely examples, and that other vectors and combinations may be used within the spirit and scope of the disclosure.

FIG. 1 is a schematic diagram of one embodiment of an exemplary SICD system 100 that may be used to terminate VT in a heart 101 of a subject 103. SICD system 100 includes a case 102, a first conductive lead 104, and a second conductive lead 106 extending from case 102. First conductive lead 104 includes a first coil electrode 108 and a second coil electrode 110. Further, second conductive lead 106 includes a third coil electrode 112 and a fourth coil electrode 114. First coil electrode 108 and second coil electrode 110 may be, for example, portions (e.g., halves) of a single linear defibrillation coil on first conductive lead 104. Third coil electrode 112 and fourth coil electrode 114 may similarly be portions (e.g., halves) of a single linear defibrillation coil on second conductive lead 106.

In this embodiment, first coil electrode 108 and second coil electrode 110 are anterior of heart 101, and second conductive lead 106 wraps around a side of the patient such that fourth coil electrode 114 is posterior of heart 101. Further, first coil electrode 108 and second coil electrode 110 are oriented generally orthogonally to fourth coil electrode 114. Alternatively, the case and coils of SICD system 100 may have any suitable position and orientation. For example, in some embodiments, first coil electrode 108 is positioned closer to case 102, and second coil electrode 110 is positioned approximately where first coil electrode is shown in FIG. 1. In yet another embodiment, first coil electrode 108, second coil electrode 110, third coil electrode 112, and fourth coil electrode 114 are all included on a single lead that beings at case 102, runs along the stemum, turns when proximate the xiphoid process, and wraps around to the side and back to place the coil electrodes in positions similar to those shown in FIG. 1.

In this embodiment, ATP may be achieved using first coil electrode 108, second coil electrode 110, or a combination of first coil electrode 108 and second coil electrode 110. Further, an evoked response may be detected using other combinations of the coils of SICD system 100. For example, the following Table 1 lists several example pacing vectors and paced evoked response sensing electrode combinations. The numbers listed in Table 1 correspond to the part numbers of the components.

TABLE 1

| Pacing (Cathode to Anode) | Paced Evoked Response Sensing Electrode Combinations |
|---|---|
| 110 to 102 | 108 to (112 and/or 114) |
| 108 to 102 | 110 to (112 and/or 114) |
| 110 to (112 and 114) | 108 to 102 |
| 108 to (112 and 114) | 110 to 102 |
| 108 to 110 | 102 to (112 and 114) |
| 110 to 108 | 102 to (112 and 114) |

In some embodiments, the electrode combination that provides a smallest accelerometer signal (e.g., detected using an accelerometer in case 102) is used for ATP (i.e., that combination is automatically selected by the controller). This facilitates reducing unnecessary skeletal muscle stimulation. Further, in some embodiments, SICD system 100 may automatically analyze (using the controller) which electrode combination detects the largest evoked response and automatically use this combination for evoked response detection. Further, if no evoked response is detected, the amplitude of the ATP pulses may be increased.

The following Table 2 lists several example electrode configurations for biphasic defibrillation pulse delivery with low DFT. Further, Table 2 lists corresponding electrode combinations for dual vector sensing.

TABLE 2

| Defibrillation Shocking | Discrimination Sensing (Dual Vector) | |
|---|---|---|
| (102 and 108 and 110) to (112 and 114) | 108 to 110 | (112 and 114) to 102 |
| (102 and 108 and 110) to (112 and 114) | 108 to 102 | (112 and 114) to 102 |
| (102 and 108 and 110) to (112 and 114) | 110 to 102 | (112 and 114) to 102 |
| (102 and 108 and 110) to (112 and 114) | 110 to (112 and 114) | (112 and 114) to 102 |
| (102 and 108 and 110) to (112 and 114) | 108 to (112 and 114) | (112 and 114) to 102 |

Because myopotentials may be generated by skeletal muscle contraction on one vector and not the other, a cross-correlation is performed between the two sensing vectors to increase the signal to noise ratio in such situations. See, for example, U.S. Pat. Nos. 7,970,473, and 7,447,540, both of which are incorporated herein by reference in their entirety. Further, in some embodiments, sensing vectors that provide a largest R-wave and/or a largest R-wave to T-wave ratio may be automatically selected to reduce the probability of under-sensing R-waves and over-sensing T-waves.

FIG. 2 is a schematic diagram of another embodiment of an exemplary SICD system 200 that may be used to terminate VT in heart 101 of subject 103. SICD system 200 includes a case 202, a first conductive lead 204, and a second conductive lead 206 extending from case 202. First conductive lead 204 includes a first coil electrode 208 and a second coil electrode 210. Further, second conductive lead 206 includes a third coil electrode 212 and a fourth coil electrode 214. First coil electrode 208 and second coil electrode 210 may be, for example, portions (e.g., halves) of a single linear defibrillation coil on first conductive lead 204. Third coil electrode 212 and fourth coil electrode 214 may similarly be portions (e.g., halves) of a single linear defibrillation coil on second conductive lead 206.

In this embodiment, first coil electrode 208 and second coil electrode 210 are anterior of heart 101, and second conductive lead 206 wraps around a side of the patient such that fourth coil electrode 214 is posterior of heart 101.

Further, first coil electrode 208 and second coil electrode 210 are oriented generally parallel to fourth coil electrode 214. Alternatively, the case and coils of SICD system 200 may have any suitable position and orientation. For example, in some embodiments, case 202 may be located in a mid-axillary position, on the left.

In this embodiment, ATP may be achieved using first coil electrode 208, second coil electrode 210, or a combination of first coil electrode 208 and second coil electrode 210. Further, evoked response may be detected using other combinations of the coils of SICD system 200. For example, the following Table 3 lists several example pacing vectors and paced evoked response sensing electrode combinations. The numbers listed in Table 3 correspond to the part numbers of the components.

TABLE 3

| Pacing (Cathode to Anode) | Paced Evoked Response Sensing Electrode Combinations |
| --- | --- |
| 210 to 202 | 208 to (212 and/or 214) |
| 208 to 202 | 210 to (212 and/or 214) |
| 210 to (212 and 214) | 208 to 202 |
| 208 to (212 and 214) | 210 to 202 |
| 208 to 214 | 202 to 212 |
| 210 to 212 | 202 to 214 |

As with SICD system 100, in some embodiments, the electrode combination that provides a smallest accelerometer signal (e.g., detected using an accelerometer in case 202) is used for ATP. This facilitates reducing unnecessary skeletal muscle stimulation. Further, in some embodiments, SICD system 200 may automatically analyze which electrode combination detects the largest evoked response and automatically use this combination for evoked response detection. Further, if no evoked response is detected, the amplitude of the ATP pulses may be increased.

The following Table 4 lists several example electrode configurations for biphasic defibrillation pulse delivery with low DFT. Further, Table 4 lists corresponding electrode combinations for dual vector sensing.

TABLE 4

| Defibrillation Shocking | Discrimination Sensing (Dual Vector) | |
| --- | --- | --- |
| (214 and 210 and 208) to 202 | 208 to 210 | 214 to 202 |
| (214 and 210 and 208) to 202 | 208 to 202 | 214 to 202 |
| (214 and 210 and 208) to 202 | 210 to 202 | 214 to 202 |
| (214 and 210 and 208) to 202 | 210 to 214 | 208 to 214 |
| (214 and 210 and 208) to 202 | 210 to 202 | 208 to 214 |
| (214 and 210 and 208) to 202 | 208 to 202 | 210 to 214 |

FIG. 3 is a schematic diagram of another embodiment of an exemplary SICD system 300 that may be used to terminate VT in heart 101 of subject 103. SICD system 300 includes a case 302 and a first conductive lead 304 extending from case 302. First conductive lead 304 includes a first coil electrode 308, a second coil electrode 310, and a third coil electrode 312. First coil electrode 308, second coil electrode 310, and third coil electrode 312 may be, for example, portions (e.g., thirds) of a single linear defibrillation coil on first conductive lead 304.

In this embodiment, first coil electrode 308, second coil electrode 310, and third coil electrode 312 are anterior of heart 101. Further, first coil electrode 208 is oriented generally parallel to second coil electrode 310 and third coil electrode 312. Alternatively, the case and coils of SICD system 300 may have any suitable position and orientation.

For example, in some embodiments, first coil electrode 308 may be segmented into two separate coils.

In this embodiment, ATP may be achieved using first coil electrode 308, second coil electrode 310, third coil electrode 312, or a combination of at least two of first coil electrode 308, second coil electrode 310, third coil electrode 312. Further, evoked response may be detected using other combinations of the coils of SICD system 300. For example, the following Table 5 lists several example pacing vectors and paced evoked response sensing electrode combinations. The numbers listed in Table 5 correspond to the part numbers of the components.

TABLE 5

| Pacing (Cathode to Anode) | Paced Evoked Response Sensing Electrode Combinations |
| --- | --- |
| 308 to 302 | 310 to 312 |
| 310 to 302 | 308 to 312 |
| 312 to 302 | 308 to 310 |

As with SICD system 100, in some embodiments, the electrode combination that provides a smallest accelerometer signal (e.g., detected using an accelerometer in case 302) is used for ATP. This facilitates reducing unnecessary skeletal muscle stimulation. Further, in some embodiments, SICD system 300 may automatically analyze which electrode combination detects the largest evoked response and automatically use this combination for evoked response detection. Further, if no evoked response is detected, the amplitude of the ATP pulses may be increased.

The following Table 6 lists several example electrode configurations for biphasic defibrillation pulse delivery with low DFT. Further, Table 6 lists corresponding electrode combinations for dual vector sensing.

TABLE 6

| Defibrillation Shocking | Discrimination Sensing (Dual Vector) | |
| --- | --- | --- |
| (308 and 310 and 312) to 302 | 310 to 312 | 308 to 302 |
| (308 and 310 and 312) to 302 | 310 to 302 | 308 to 312 |
| (308 and 310 and 312) to 302 | 308 to 302 | 310 to 312 |
| (308 and 310 and 312) to 302 | 312 to 302 | 308 to 310 |

Figure 4:
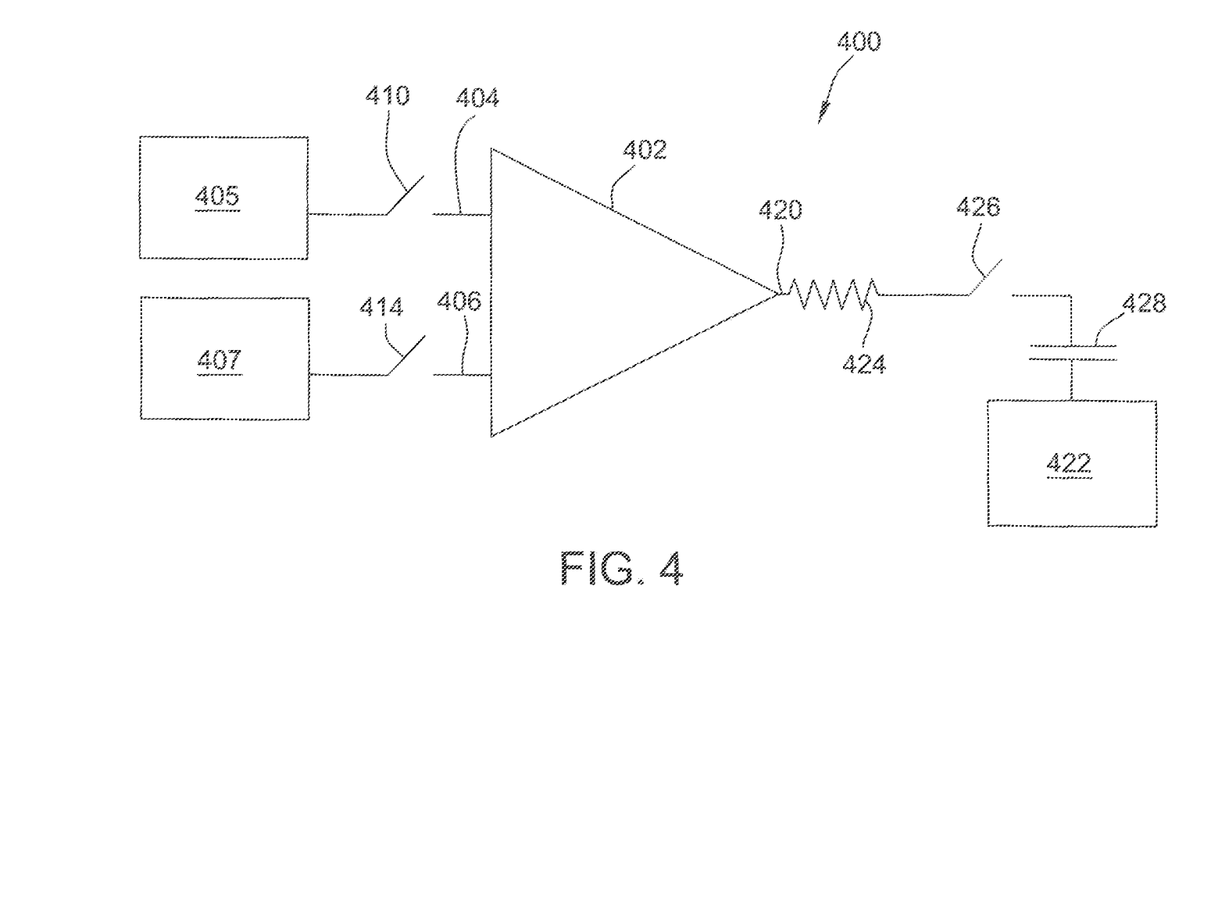
FIG. 4 is a circuit diagram of one embodiment of signal processing circuitry including a sense amplifier.

When applying ATP using a SICD system (such as SICD systems 100, 200, and 300), to prevent sensing relatively large pacing pulse artifacts, a sense amplifier is blanked (i.e., prevented from sensing) just before delivery of pacing pulses. For example, FIG. 4 is a circuit diagram of one embodiment of signal processing circuitry 400 including a sense amplifier 402. Signal processing circuitry 400 may be included within a case, such as cases 102, 202, and 302 (shown in FIGS. 1-3).

As shown in FIG. 4, sense amplifier 402 includes a first input 404 connected to a sensing electrode 405 and a second input 406 connected to a reference electrode 407. Further, a first input switch 410 is connected between first input 404 and sensing electrode 405, and a second input switch 414 is connected between second input 406 and reference electrode 407. In this embodiment, sensing electrode 405 and reference electrode 407 are different from a pacing electrode to prevent a pacing polarization artifact from obscuring the sensed evoked response. An output 420 of sense amplifier 402 is coupled to an analog to digital converter 422 via a resistor 424, an output switch 426, and a capacitor 428.

Just prior to delivering an ATP pulse (e.g., 1 ms before delivering an ATP pulse), first input switch 410, second input switch 414, and output switch 426 are opened (e.g., using the controller). Capacitor 428 acts as a sample and hold element, retaining the measured EKG level just prior to pacing. After the pacing pulse is delivered (e.g., approximately 5 to 20 ms later), first input switch 410, second input switch 414, and output switch 426 are closed (e.g., using the controller), and sensing resumes. In this embodiment, the digitized output signal is analyzed for an evoked response by determining if the derivative of the signal exceeds a negative or positive threshold (e.g., ±0.01 mV/ms) in a predetermined time period (e.g., 175 ms after the pacing pulse).

Figure 5:
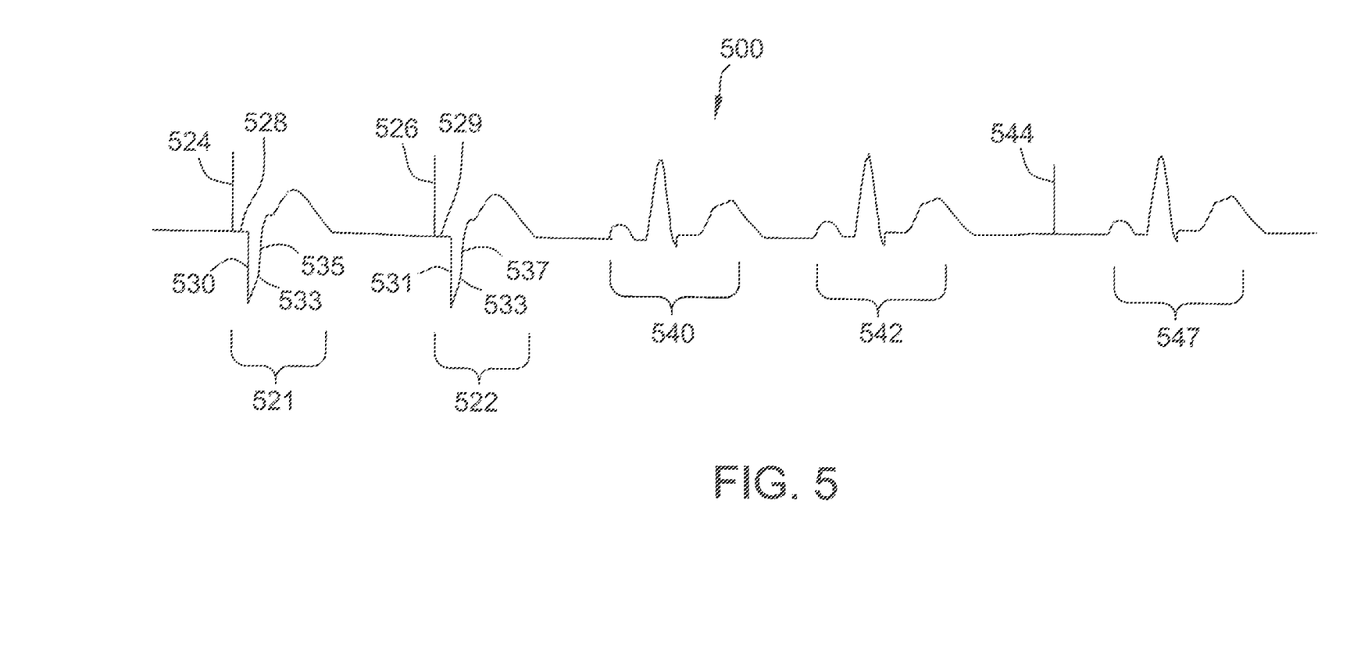
FIG. 5 is a trace of an example EKG captured using the signal processing circuitry shown in FIG. 4.

FIG. 5 is a trace of an example EKG 500 captured using signal processing circuitry 400 (shown in FIG. 4). EKG 500 includes paced QRS complexes 521 and 522. Pacing pulses 524 and 526 mark the onset of blanking, resulting in flat segments 528 and 529 following pacing pulses 524 and 526. Sudden sharp downward transitions 530 and 531 mark the end of the blanking, and occur during a mid-region of paced QRS complexes 521 and 522. The derivative of subsequent rapid upward deflections 535 and 537 can be processed to verify capture.

As shown in FIG. 5, EKG 500 further includes native QRS complexes 540 and 542 that were detected and thus inhibited pacing. Further, EKG 500 includes a pacing pulse 544 that is not followed by an evoked response. Thus, EKG 500 subsequently includes a native QRS 547 that emerges as a result of the loss of capture of pacing pulse 544.

Figure 6:
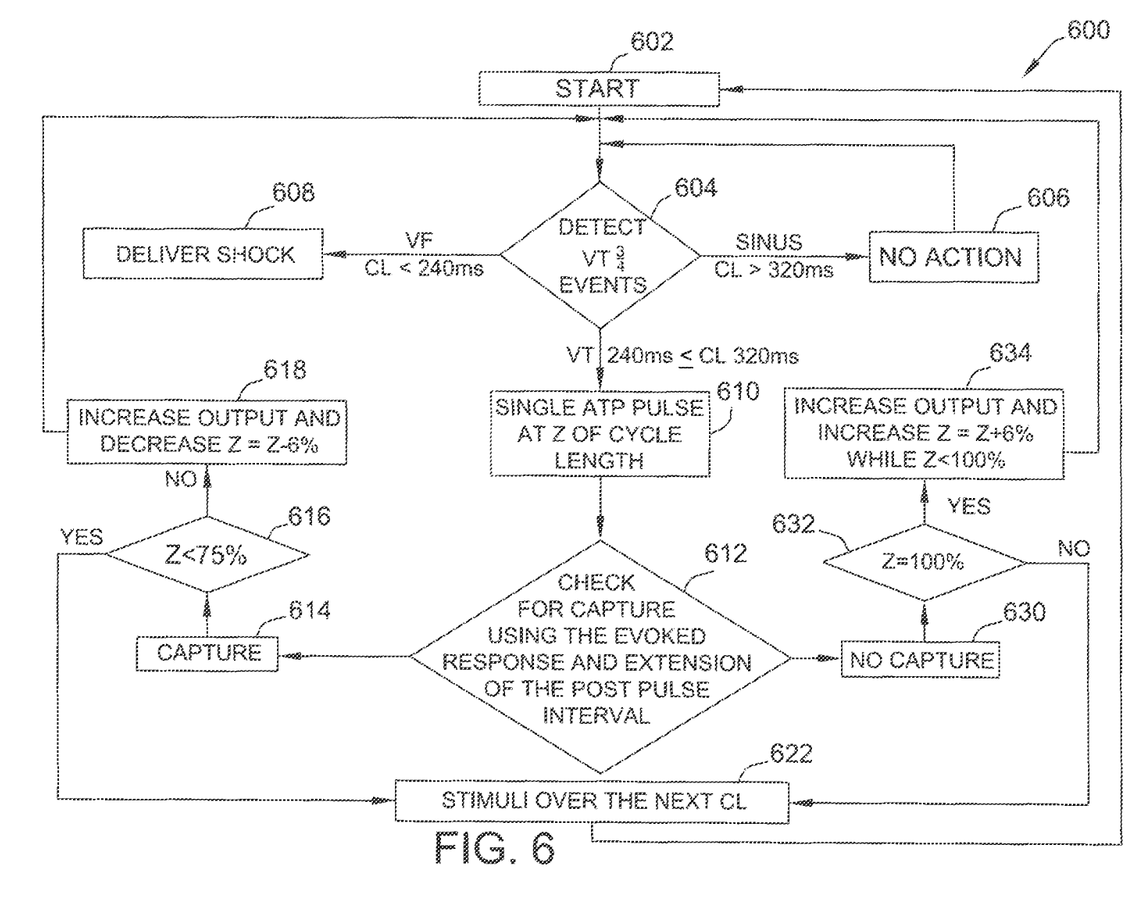
FIG. 6 is a flowchart of an algorithm for providing ATP therapy to extinguish VT with a minimal number of pacing pulses.

FIG. 6 is a flowchart of an algorithm 600 for providing ATP therapy to extinguish VT with a minimal number of pacing pulses. Algorithm 600 may be implemented, for example, using SICD systems 100, 200, and 300. Specifically, algorithm may be performed by the controller (e.g., a microprocessor) included in cases 102, 202, and 302. Algorithm 600 starts at block 602. Initially, in this embodiment, a percentage, Z, of a cycle length, CL, is set at 82%. The cycle length is defined as the time interval between subsequent R waves. Alternatively, Z may be set to any suitable value.

At block 604, is determined whether at least 3 of 4 VT events satisfy certain criteria. Alternatively, other ratios may be used (e.g., 12 of 16 events). If the cycle length is greater than 320 ms (indicating a sinus rhythm) for at least 3 of 4 events, flow proceeds to block 606, and no action is taken. If the cycle length is less than 240 ms (indicating ventricular fibrillation (VF)) for at least 3 of 4 events, flow proceeds to block 608, and a defibrillating shock is delivered. If, however, the cycle length is greater than or equal to 240 ms and less than or equal to 320 ms (indicating VT) for at least 3 of 4 events, flow proceeds to block 610, and a single ATP pulse is delivered at Z (i.e., 82%) of the cycle length following the last event.

Subsequently, at block 612, it is determined whether capture is achieved based on the evoked response and/or extension of the cycle length. If capture is achieved, flow proceeds to block 614 and subsequently to block 616, where it is determined whether Z is less than 75%. If Z is not less than 75%, flow proceeds to block 618, at which point the amplitude of subsequent ATP pulses is increased (e.g., by 20%), and Z is reduced by 6%, before flow returns to block 602. If Z is less than 75%, flow proceeds to block 622, and i) a predetermined number of ATP pulses (e.g., 4 to 5 pulses) are applied over the next cycle length at equally spaced intervals or, alternatively, ii) a predetermined number of ATP pulses (e.g., 3 to 8 pulses) are delivered at 88% of the cycle length.

At block 612, if capture is not achieved, flow proceeds to block 630 and subsequently to block 632, where it is determined whether Z is less than 100%. If Z is less than 100%, flow proceeds to block 634, at which point the amplitude of subsequent ATP pulses is increased (e.g., by 20%), and Z is increased by 6% (although keeping Z below 100%), before flow returns to block 604. If Z is not less than 100%, flow proceeds to block 622, and i) a predetermined number of ATP pulses (e.g., 4 to 5 pulses) are applied over the next cycle length at equally spaced intervals or, alternatively, ii) a predetermined number of ATP pulses (e.g., 3 to 8 pulses) are delivered at 88% of the cycle length in an attempt to achieve capture.

In the systems and methods described herein, discomfort from the applied ATP may be reduced using several techniques.

For example, in some embodiments, the amplitude of the ATP pulses can be minimized by performing capture verification using the evoked response. For example, the paced evoked response may be analyzed to perform capture verification and to determine the capture threshold (which may be, e.g., approximately 30 to 80 mA). Further, the coil electrodes may be coated with a non-polarizable coating to reduce polarization, so that immediate sensing after pacing is possible.

Further, as described above, the sense amplifier can be blanked during pacing, and a sample and hold circuit (e.g., a capacitor) can be used to hold the ECG voltage during pacing to facilitate detecting the evoked response. If the evoked response is not detected, the ATP pulse amplitude may be increased on subsequent pulses until capture is achieved and verified from the evoked response.

Further, in some embodiments, monophasic cathodic pulses are delivered instead of biphasic pulses. Monophasic cathode pulses have lower thresholds, and may be less noxious to the subject.

In addition, in some embodiments, a learning mode is implemented that is capable of recognizing a pulse regiment that is effective in achieving VT termination, and using that pulse regiment in terminate subsequent future arrhythmias. For example, if the VT has a cycle length of 300 ms, and is terminated by a 50 mA pulse at 93% of the cycle length, then the next time arrhythmia occurs, a 50 mA pulse is applied at 93% of the cycle length. Similarly, if the VT has a cycle length of 270 ms, and is terminated by a 80 mA pulse at 88% of the cycle length, then the next time arrhythmia occurs, a 80 mA pulse is applied at 88% of the cycle length.

In some embodiments, a predetermined (and programmable) number of ATP pulses are applied to attempt VT termination before shocking is implemented. Alternatively, an algorithm may be used to provide cardioversion with a predetermined number of ATP attempts.

Further, in some embodiments, an in-line pacing electrode coil may be positioned over a point of maximum impulse (e.g., a V3 lead location) or in a parasternal location. The anode that does not provide the pacing may be the case or a larger electrode than the pacing electrode. In some embodiments, the entire shocking electrode may be used to perform ATP, allowing for multisite pacing that may improve ATP efficacy in many patients. Alternatively, the shocking electrode may be divided into multiple segments, as described above. In such cases, pacing may be achieved using either segment individually or both segments combined. Further, the electrode combination that provides the lowest pacing threshold may be automatically selected using a capture verification algorithm that measures the pacing threshold. For defibrillation, the segmented pacing electrode acts as one shocking electrode. Optimizing the pacing electrode size (i.e., length) may facilitate minimizing skeletal muscle stimulation while achieving adequate length for capture. For example, each segment may have a length from approximately 3 to 6 centimeters (cm).

In addition, in some embodiments, a short coil segment is utilized for a first one or more rounds of ATP, allowing for adjustment of cycle length and/or pacing output in each consecutive ATP round. In case of failure in the first one or more rounds to terminate the VT, two or more coil segments are electrically coupled for delivering a second one or more rounds of ATP. In this scheme, the first one or more rounds elicit less skeletal muscle and/or diaphragmatic contraction, while the second one or more rounds more aggressively attempt to capture ventricular myocardium to penetrate into the VT circuit, with less regard for skeletal muscle and/or diaphragmatic contraction.

In some embodiments, a time optimization of ATP pulse delivery is controlled to coincide with spatial optimization. Spatial optimization may be controlled largely by selection of one or more stimulating electrodes. Specifically, the smaller the electrode and the closer to the myocardium, the more the electrode behaves like a point stimulator. In contrast, the larger the electrode and the further from the myocardium, the more the electrode behaves like a field stimulator. Field stimulation, at a tissue level, may result in multiple coordinated yet spatially distributed stimulation capture locations.

For example, suppose a first ATP attempt uses a single short coil segment at a low-to-moderate stimulation amplitude. This would be expected to result in a virtual point stimulation. If the first ATP attempt fails to terminate the VT, modulation of timing with regard to cycle length can be performed (e.g., as described in associated with FIG. 6). In some embodiments, subsequent ATP use one or more coil segments with larger dimensions than the coil segment of the first ATP attempt. Because of the larger size, the excitation at the same total energy will achieve stimulation that is more like field stimulation, which is more spatially diverse. Thus, when switching to a larger electrode, the Z value may be increased. Similarly, when switching to a larger coil length to reduce energy delivered (e.g., to avoid excessive stimulation of skeletal muscle), the Z value may be decreased accordingly.

Figure 7:
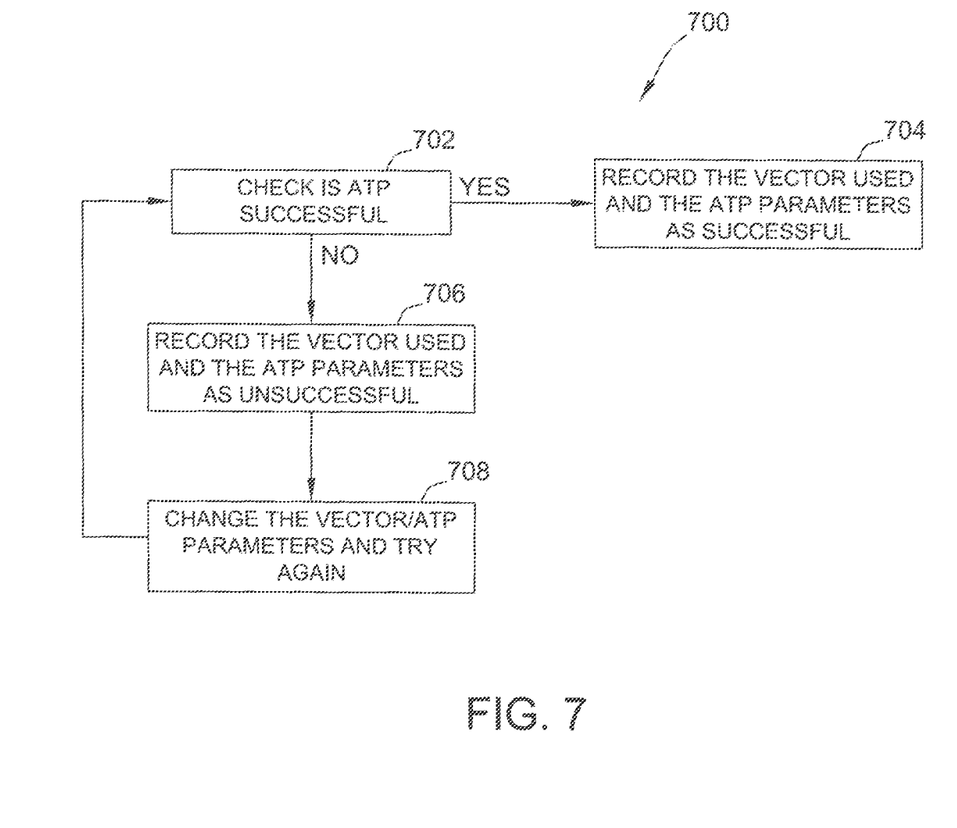
FIG. 7 is a flowchart of an algorithm for providing ATP therapy to extinguish VT that incorporates a learning mode.

For example, FIG. 7 is a flowchart of an algorithm 700 for providing ATP therapy to extinguish VT that incorporates a learning mode. Algorithm 700 may be implemented, for example, using SICD systems 100, 200, and 300. Specifically, algorithm may be performed by the controller (e.g., a microprocessor) included in cases 102, 202, and 302. Further algorithm 700 may be implemented in combination with algorithm 600 (shown in FIG. 6).

At block 702, after ATP is applied using a particular vector and stimulation parameters, it is determined whether the ATP was successful in terminating VT. If the ATP was successful, flow proceeds to block 704, and the vector and stimulation parameters that were used in the ATP are recorded (i.e., stored) with an indication that the vector and stimulation parameters successfully terminated VT. Then, for future episodes, the recorded vector and stimulation parameters that previously resulted in terminating VT can be retrieved, and ATP is again applied using that same vector and stimulation parameters.

If, however, at block 702, the ATP was not successful, flow proceeds to block 706, and the vector and stimulation parameters are recorded with an indication that they were unsuccessful. Then, at block 708, at least one of the vector and the stimulation parameters are modified and ATP is applied again. Flow then returns to block 702 to determine whether this ATP was successful.

Accordingly, the systems and methods described herein facilitate applying anti-tachycardia pacing ATP to treat VT using subcutaneous implantable cardioverter-defibrillators SICDs. An SICD implantable in a subject includes a case including a controller, and at least one conductive lead extending from the case. The at least one conductive lead includes a plurality of coil electrodes, wherein the SICD is configured, via the controller, to apply anti-tachycardia pacing (ATP) to the subject using the at least one conductive lead. Further, those of skill in the art will appreciate that, in some embodiments, the electrodes of the SICD (and the electrode configurations described herein) may also be used to apply high voltage (HV) therapy.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A subcutaneous implantable cardioverter-defibrillator (SICD) comprising:
one or more leads configured to be implanted in a subcutaneous region of a subject, the one or more leads including multiple electrodes;
a case forming one of the multiple electrodes;
sensing circuitry; and
a controller configured to:
apply anti-tachycardia pacing (ATP) therapy to the subject via a pacing combination of electrodes at a first time, the pacing combination of electrodes comprising two or more of the multiple electrodes;
connect the sensing circuitry to a first sensing combination of electrodes, the first sensing combination of electrodes comprising two or more of the multiple electrodes;

sense, via the first sensing combination of electrodes, a first paced evoked response that is responsive to the ATP therapy applied at the first time;

apply anti-tachycardia pacing (ATP) therapy to the subject via a same or different pacing combination of electrodes at a second time;

connect the sensing circuitry to a second sensing combination of electrodes, the second sensing combination of electrodes comprising two or more of the multiple electrodes;

sense, via the second sensing combination of electrodes, a second paced evoked response that is responsive to the ATP therapy applied at the second time;

determine sizes of the first and second paced evoked responses; and select one of the first sensing combination of electrodes or the second sensing combination of electrodes to use for subsequent evoked response detection based on the sizes of the first and second paced evoked responses.

2. The SICD of claim 1, further comprising an accelerometer configured to sense accelerometer signals, wherein the pacing combination of electrodes used by the controller to apply the ATP therapy at the first time is a first ATP combination of electrodes, and the controller is configured to use a second ATP combination of electrodes to apply the ATP therapy at the second time, the second ATP combination of electrodes comprising two or more of the multiple electrodes, wherein the controller is configured to:

obtain first accelerometer signals responsive to applying the ATP therapy via the first ATP combination of electrodes;

obtain second accelerometer signals responsive to applying the ATP therapy via the second ATP combination of electrodes;

determine sizes of the first and second accelerometer signals; and select one of the first ATP combination of electrodes or the second ATP combination of electrodes to use for delivery of subsequent ATP therapy based on the sizes of the first and second accelerometer signals.

3. The SICD of claim 1, wherein the controller is configured to apply the ATP therapy at the first time and the second time by delivering pacing pulses having an amplitude from approximately 20 to 200 milliamps and a pulse width from approximately 4 to 40 milliseconds.

4. The SICD of claim 1, wherein the one or more leads include a first lead and a second lead, the first lead comprising a first coil electrode and a second coil electrode, and the second lead comprising a third coil electrode and a fourth coil electrode.

5. The SICD of claim 4, wherein the first coil electrode and the second coil electrode are portions of a single linear defibrillation coil.

6. The SICD of claim 4, wherein the SICD is configured to be implanted such that the first and second coil electrodes are anterior of a heart of the subject, and the fourth coil electrode is posterior of the heart of the subject.

7. The SICD of claim 1, wherein the first sensing combination of electrodes includes a coil electrode of a first lead of the one or more leads representing a cathode and the case representing an anode.

8. The SICD of claim 1, wherein the one or more leads include a first lead comprising a first coil electrode, a second coil electrode, and a third coil electrode.

9. The SICD of claim 1, wherein the sensing circuitry comprises a sense amplifier and a plurality of switches, and wherein the controller is configured to open the plurality of switches prior to delivery of a pacing pulse of the ATP therapy to prevent sensing of pacing pulse artifacts.

10. The SICD of claim 1, wherein the controller is configured to cause ATP pacing pulses to be delivered at a predetermined percentage of a cardiac cycle length, and wherein the controller is configured to adjust at least one of an output intensity or the predetermined percentage for subsequent ATP pacing pulses based at least in part on whether capture is achieved.

11. The SICD of claim 1, wherein the controller is configured to select the first sensing combination of electrodes for the subsequent evoked response detection based on the size of the first paced evoked response being larger than the size of the second paced evoked response.

12. A subcutaneous implantable cardioverter-defibrillator (SICD) comprising:

one or more leads configured to be implanted in a subcutaneous region of a subject, the one or more leads including multiple electrodes;

a case forming one of the multiple electrodes;

an accelerometer configured to sense accelerometer signals; and a controller configured to:

apply anti-tachycardia pacing (ATP) therapy to the subject at a first time, via a first ATP combination of electrodes, the first ATP combination of electrodes comprising two or more of the multiple electrodes;

obtain first accelerometer signals responsive to applying the ATP therapy via the first ATP combination of electrodes;

apply ATP therapy to the subject at a second time, via a second ATP combination of electrodes, the second ATP combination of electrodes comprising two or more of the multiple electrodes;

obtain second accelerometer signals responsive to applying the ATP therapy via the second ATP combination of electrodes;

determine sizes of the first and second accelerometer signals; and select one of the first ATP combination of electrodes or the second ATP combination of electrodes to use for delivery of subsequent ATP therapy based on the sizes of the first and second accelerometer signals.

13. The SICD of claim 12, wherein the controller is configured to select the first ATP combination of electrodes to use for delivery of the subsequent ATP therapy based on the size of the first accelerometer signals being smaller than the size of the second accelerometer signals.

14. The SICD of claim 12, wherein the controller is configured to apply the ATP therapy at the first time and the second time by delivering pacing pulses having an amplitude from approximately 20 to 200 milliamps and a pulse width from approximately 4 to 40 milliseconds.

15. The SICD of claim 12, wherein the one or more leads include a first lead and a second lead, the first lead comprising a first coil electrode and a second coil electrode, and the second lead comprising a third coil electrode and a fourth coil electrode.

16. The SICD of claim 15, wherein the first coil electrode and the second coil electrode are portions of a single linear defibrillation coil.

17. The SICD of claim 15, wherein the SICD is configured to be implanted such that the first and second coil electrodes are anterior of a heart of the subject, and the fourth coil electrode is posterior of the heart of the subject.

18. The SICD of claim 12, wherein the first ATP combination of electrodes includes a coil electrode of a first lead of the one or more leads representing a cathode and the case representing an anode.

19. The SICD of claim 12, wherein the one or more leads include a first lead comprising a first coil electrode, a second coil electrode, and a third coil electrode.

20. The SICD of claim 12, wherein the case further comprises sensing circuitry comprising a sense amplifier and a plurality of switches, and wherein the controller is configured to open the plurality of switches prior to delivery of a pacing pulse of the ATP therapy to prevent sensing of pacing pulse artifacts.

21. The SICD of claim 12, wherein the controller is configured to cause ATP pacing pulses to be delivered at a predetermined percentage of a cardiac cycle length, and wherein the controller is configured to adjust at least one of an output intensity or the predetermined percentage for subsequent ATP pacing pulses based at least in part on whether capture is achieved.

22. The SICD of claim 12, further comprising sensing circuitry, the controller configured to:
 connect the sensing circuitry to a first sensing combination of electrodes, the first sensing combination of electrodes comprising two or more of the multiple electrodes;
 sense, via the first sensing combination of electrodes, a first paced evoked response that is responsive to the ATP therapy applied at the first time;
 connect the sensing circuitry to a second sensing combination of electrodes, the second sensing combination of electrodes comprising two or more of the multiple electrodes;
 sense, via the second sensing combination of electrodes, a second paced evoked response that is responsive to the ATP therapy applied at the second time;
 determine sizes of the first and second paced evoked responses; and
 select one of the first sensing combination of electrodes or the second sensing combination of electrodes to use for subsequent evoked response detection based on the sizes of the first and second paced evoked responses.

\* \* \* \* \*